United States Patent [19]

Uzgiris

[11] Patent Number: 4,634,599

[45] Date of Patent: Jan. 6, 1987

[54] METHOD FOR MAKING ORDERED MONOLAYERS OF MACROMOLECULES

[75] Inventor: Egidijus E. Uzgiris, Schenectady, N.Y.

[73] Assignee: General Electric Company, Schenectady, N.Y.

[21] Appl. No.: 729,609

[22] Filed: May 2, 1985

[51] Int. Cl.[4] ............................ A01N 1/02; B32B 9/00
[52] U.S. Cl. ............................................. 427/2; 378/73; 424/88; 428/408; 428/420; 428/478.2; 435/7
[58] Field of Search .................. 260/112 R, 112 B; 378/73; 424/88; 427/2; 428/408, 420, 478.2; 435/7

[56] References Cited

U.S. PATENT DOCUMENTS 4,172,827 10/1979 Giaever ............................ 424/88 X
4,489,133 12/1984 Kornberg ............................ 428/408

OTHER PUBLICATIONS

Two-Dimensional Crystallization Technique for Imaging Macromolecules, with Application to Antigen-Antibody-Complement Complexes, Uzgiris et al., reprinted from Nature, vol. 301, No. 5896, pp. 134-136 (1/13/83).

*Primary Examiner*—Michael R. Lusignan
*Attorney, Agent, or Firm*—William A. Teoli; James C. Davis, Jr.; James Magee, Jr.

[57] ABSTRACT

A method is provided for making ordered monolayers of macromolecules. A supported lipid polylayer is contacted with macromolecules in an aqueous polar solution and allowed to incubate.

6 Claims, 2 Drawing Figures

METHOD FOR MAKING ORDERED MONOLAYERS OF MACROMOLECULES

BACKGROUND OF THE INVENTION

Prior to the present invention, as shown by Uzgiris et al., Two-Dimensional Crystallization Technique for Imaging Macromolecules, With Application to Antigen-Antibody-Complement Complexes, Nature, Vol. 31, No. 5896, pp. 134–136, January 1983 and Kornberg, U.S. Pat. No. 4,489,133, a technique for effecting two-dimensional crystallization of macromolecules as an ordered monolayer were available. Two-dimensional ordering of organic polar solvent soluble organic macromolecules, such as poly(amino acids), was achieved by Kornberg by placing a supported lipid monolayer in a polar solution of the organic macromolecules. The organic macromolecules were allowed to incubate for a sufficient period of time to effect their two-dimensional crystallization.

Although valuable results have been achieved by the method of U.S. Pat. No. 4,489,133, for particular macromolecules, such as antibody IgG, effective results have not been found for growing a wide variety of other macromolecules as ordered monolayers. Experience has shown that the lipid monolayer of Kornberg has a tendency to separate too quickly from its supporting substrate before a sufficient incubation period has been achieved to allow sufficient nucleation. In addition, even though limited success has been achieved with growing ordered monolayers of IgG, the linear crystalline patterns of IgG macromolecules were often irregularly spaced as observed under an electron microscope due to insufficient lipid substrate support. It would be desirable, therefore, to provide a supported lipid substrate capable of allowing sufficient incubation time while in an aqueous medium, to effect the nucleation of a wide variety of macromolecular ordered monolayers.

The present invention is based on the discovery that a lipid polylayer having at least two hydrophilic regions and at least one lipophilic region and supported on one of its hydrophilic regions by a hydrophilic substrate, can provide significantly improved two-dimensional crystallization of a wide variety of macromolecules, as compared to results achieved with a lipid monolayer.

STATEMENT OF THE INVENTION

There is provided by the present invention, a method for effecting the nucleation of macromolecules as an ordered monolayer on a hydrophilic region of a supported lipid polylayer having at least two hydrophilic regions and an interior lipophilic region comprising, (1) effecting contact between macromolecules and a hydrophilic region of the lipid polylayer in an aqueous medium and (2) incubating the resulting mixture for a time sufficient to allow for the ordering of such macromolecules, where the lipid polylayer is anchored onto a supporting hydrophilic substrate through one of its hydrophilic regions.

Lipids which can be utilized in the practice of the present invention are preferably phospholipids derived from either glycerol, which are more specifically phosphoglycerides having a glycerol backbone, two fatty acid chains, referred to sometimes as the "lipophilic region", and a phosphorylated alcohol, referred to sometimes as "hydrophilic region", or "polar head group". Additional phospholipids which can be used are phospholipids derived from sphingosine. In addition to phospholipids, glycolipids and cholesterol also can be utilized. Specific phospholipids which are preferred are, for example, N-dinitrophenylphosphatidylcaproylethanolamine, N-dinitrophenylaminocaproyl phosphatidylethanolamine, etc. Additional phospholipids, glycolipids and cholesterol lipids, which can be used in the practice of the invention, are further shown in Stryer, Biochemistry (Second Edition), pages 206–212, W.H. Freeman and Company, New York, 1981, and Ullman et al., U.S. Pat. No. 4,193,983, incorporated herein by reference.

To further illustrate the practice of the present invention, reference is made to FIG. 1 showing a lipid bilayer supported by a substrate, referred to hereinafter as the "bilayer-substrate composite" or "composite".

More particularly, there is shown in FIG. 1, a supporting substrate at 10, polar head groups at 20 and 21, and fatty acid chains at 30 and 31.

Substrates which can be used in the practice of the present invention to make the composite are, for example, nitrocellulose films, Formvar resin film, carbon coated films of such materials, and thermoplastic films such as Lexan ® polycarbonate, Noryl ® resin, Ultem ® polyetherimide, etc.

One method of making the composite of FIG. 1, is by initially spreading a lipid monolayer on an air-water interface. A Teflon ® resin trough can be used to receive a few drops of the lipid which is generally provided in an organic solvent, such as hexane or chloroform. A substrate, for example, a silver grid used in electron microscope studies, can be coated with colloidion and thereafter carbon shadowed using a carbon-arc deposition procedure. The carbon treated substrate can be rendered hydrophilic by exposure to U.V. An effective UV treatment is exposure to a UV lamp (Hanovia Type SH) at a distance of 3 inches for 4 minutes under atmospheric conditions.

The resulting hydrophilic carbon coated grid can be passed through the lipid monolayer and the air-water interface in the Teflon ® resin trough to effect the deposition of the lipid monolayer on the hydrophilic carbon-coated silver grid surface. The deposited lipid monolayer has its fatty-acid chains facing the aqueous media and its polar head groups abutting the hydrophilic carbon coated silver grid.

The procedure can be repeated using the lipid monolayer carbon coated silver grid. By passing the lipid monolayer coated silver grid through the Teflon ® resin trough having a lipid monolayer on the air-water interface, a bilayer and substrate composite is formed having a lipid bilayer with an interior lipophilic region and exterior hydrophilic regions. This procedure can be repeated several times if desired to build additional lipid layers.

The lipid polylayer-substrate composite can be allowed to dry or can be used directly prior to contact with macromolecules in an aqueous polar medium. Temperatures in the range of from about 0° C. to 70° C. can be employed during the incubation period. The conditions utilized in effecting the formation of the ordered macromolecular monolayer will vary widely depending upon the nature of the macromolecules. Accordingly, buffers such as 150 mM NaCl and 25 mM tris(hydroxymethyl)aminomethane, or 150 mM NaCl and 25 mM bis(2-hydroxyhydroxyethyl)imino tris(hydroxymethyl)methane can be used. The salt concentration can be varied from 50 mM to 400 mM NaCl and the buffer concentration from 0 to 75 mM. In pure salt solutions the desired pH is reached by addition of NaOH or HCl. Other common buffers which can be used are 150 mM NaCl with 25 mM [4-(2-hydroxyethyl)-1-piperazineethanesulfonic acid](HEPES). The aforementioned buffers can be added to the mixture as well as other ingredients to vary the ionic strengths, viscosity and the like.

The concentration of the macromolecule in the aqueous media can vary widely and range from 1 microgram to several milligrams, per ml. of aqueous mixture.

Macromolecules which can be nucleated as ordered monolayers in the practice of the present invention are, for example, organic molecules having molecular weights of at least about 1,000 and up to about 1,000,000 or more. Macromolecules of particular interest are the polyamino acids as exemplified by polypeptides and proteins. There can be preferably employed antibodies such as IgG, IgM, IgA, IgE, enzymes and naturally occurring receptors such as avidin, cell surface receptors and histones. Another class of macromolecules which are of interest are polynucleotides or nucleic acids which can include DNA or RNA, where the DNA may be chromasonal, plasmid, viral and where the RNA can be messenger RNA, transfer RNA, ribosomal, synthetic, etc. In addition to being organic, the macromolecules also can include organometallics, such as organosilicon materials.

In order to provide supported monomolecular layer growth, the macromolecule preferably should have sufficient solubility in a polar solvent which also allows for the formation of the lipid surfactant monolayer. Generally, the polar solvent are miscible with water and are employed in combination thereto. The organic solvent will generally not exceed 10 volume percent of the total aqueous polar solvent medium. Some of the organic solvents include, for example, alcohols such as methanol and ethanol, amides such as N,N-dimethylformamide, ketones for example acetone. In particular instances, organic solvents can be employed having only moderate water solubility.

Multiple monolayers of macromolecules can be nucleated in an ordered manner by using the monolayer incubated in accordance with the method of the present invention as a substrate. For example, the bonding of a different antibody to an IgG ordered monolayer is based on the recognition of some exposed domain of the IgG antibody.

Separation of macromolecular arrays can be effected in particular instances by adjusting the pH of the incubating bath to achieve acidic conditions. In instances where the lipid layer is made from a phospholipid, release of the ordered macromolecular layer therefrom can be achieved by use of high salt concentrations in the incubating bath.

In order that those skilled in the art will be better able to practice the present invention, the following example is given by way of illustration and not by way of limitation. All parts are by weight.

EXAMPLE 1

Figure 1:
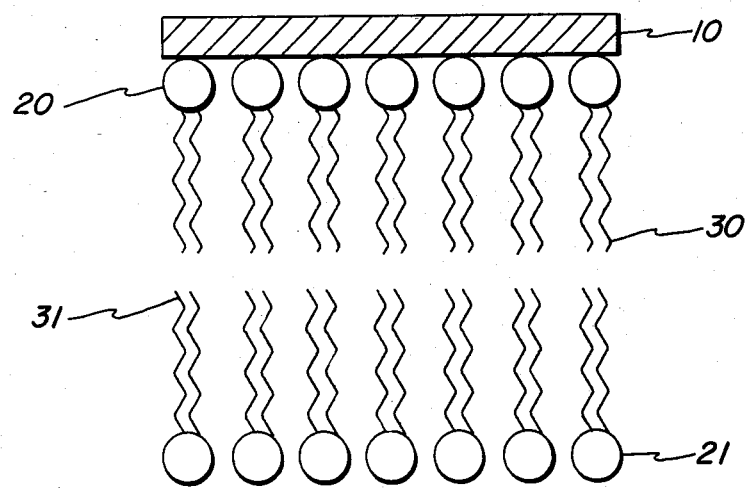
FIG. 1 shows a phospholipid bilayer securely anchored onto a hydrophillic carbon grid surface, an interior lipophilic region and an exterior hydrophilic region.

Circular silver grids, obtained from the Ladd Research Company, having a diameter of 3 mm and a thickness of 40μ were placed on a thin sheet of nitrocellulose that had been cast on a glass slide and then floated onto a water/air interface. The grids with the nitrocellulose sheet was then picked up onto a paper strip by dipping the assembly through the water surface and then withdrawing it vertically. The coated grids were then shadowed with vapor deposited carbon utilizing carbon arcs in a relatively clean high vacuum system. The carbon coated grids were then exposed for $\neq 4$ minutes under a Hanovia Type SH UV lamp at a distance of 3 inches in the air. The UV treated carbon coated silver grids were found to be hydrophilic as they wet readily upon being immersed in water. A monolayer of N-dinitrophenylaminocaproylphosphatidylethanolamine was spread as a monolayer on the air/water interface in a Teflon ® resin trough. The hydrophilic carbon coated silver grid was then passed through the spread monolayer. A composite of the silver grid and monolayer was formed with phospholipid heads abutting the hydrophilic carbon coated silver grid surface and the hydrocarbon chains exposed to the air. The composite was then reinserted through the same phospholipid monolayer resulting in the deposition of a second monolayer with a reverse orientation. The resulting composite was removed having a phospholipid bilayer securely anchored onto the hydrophilic carbon grid surface, an interior lipophilic region and an exterior hydrophilic region as shown by FIG. 1.

The composite was then floated on an aqueous solution of IgG (mouse monoclonal anti-DNP $IgG_1$) having a concentration of about 100 μg/ml. in 150 mM NaCl and 50 mM of tris(hydroxymethyl)aminomethane at a pH of 7.4. Incubation was allowed to proceed from ½ to 12 hours at a temperature in the range of from 4° C. to 60° C. The composite was then removed from the IgG solution and placed on a drop of staining solution (1% uranyl acetate), for 30 seconds. The uranyl acetate was then drained off and the composite was allowed to dry. The composite was then examined in a Hitachi 600 electron microscope. It was found that extensive 2-D crystallization had taken place. Linear patterns were observed with lateral spacing of 150 Angstroms as well as hexagonal arrays with next nearest neighbor distances of 150 Angstroms.

At low magnification, crystalline arrays of either hexagonal or linear type covered the entire grid. The fraction of the grid area that was ordered was in excess of 90%. Essentially uniform molecular sheets were observed organized into multidomain structures. The mean domain size of hexagonal order was about several μm in extent, with perhaps several thousand units all arranged along fault-free lattice lines. The domains merged along lattice fault lines to give a nearly complete coverage of the surface.

The hexagonal arrays consisted of protein clusters of 6 fold symmetry spaced about 150 Angstroms apart in a hexagonal lattice. The linear arrays consisted of chains of tightly packed molecules (periodicity of about 40 Angstroms) with a chain to chain stacking that had a 150 Angstrom repeat. In this case also, the mean domain size could be as large as several microns.

A similar procedure was followed by floating a silver grid having a lipid bilayer onto a solution of IgE. Incubation in the IgE (mouse monoclonal anti-DNP) was allowed to proceed for 6 hours. The composite was removed and stained with 1% uranyl acetate. It was found that substantially similar 2-D crystallization had occurred utilizing IgE. A fault-free, sheet like coverage of molecular clusters was observed everywhere. The clusters were organized into hexagonal arrays of similar spacing to the IgG arrays, but of less well defined local order as judged by optical diffraction. It packed into a 2-D lattice differently from the IgG antibody. The appearance of the IgE lattice was quite different; it was diffuse with few sharp edges. However, the extent of the domains was several microns, and approximately the same as IgG.

In addition to IgG and IgE, liquid-like ordered arrays, i.e. sharp nearest neighbor distance distribution for molecular clusters, but no lattice directionality to next-nearest neighbor clusters, was observed for IgG-polyclonal antibody. A similar type of packing was observed for a particular viral molecule, hemagglutanin from the influenza virus. These macromolecular monolayers also were found to be fault-free, continuous and tightly packed.

The same procedure was repeated, except that in place of the lipid bilayer in accordance with the practice of the present invention there was used a lipid monolayer prepared in accordance with the procedure of Kornberg U.S. Pat. No. 4,489,133. It was found that the patterns observed in the electron microscope were not homogenous. There were significant amounts of open areas without any antibody. The ordered domains typically occurred as isolated islands and constituted only about 15–30% of the total surface. These results were similar to the electron micrographs shown in the previously cited article in Nature, Two-Dimensional Crystallization Technique for Imaging Macromolecules, With Application to Antigen-Antibody-Complement Complexes. The data in the article indicates that 15% of the area examined was ordered, while up to 50% of the area was constituted by bright stain excluding regions which were featureless.

Figure 2:
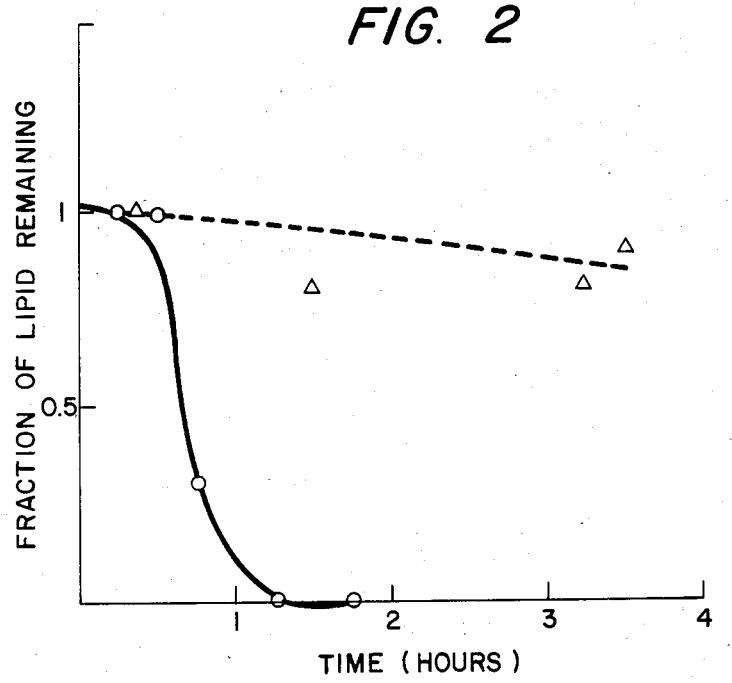
FIG. 2 shows a stability comparison between bilayers and monolayers.

FIG. 2 shows a stability comparison between bilayers and monolayers (O monolayer, Δ bilayer). The following procedure was used:

A silver grid was floated onto a saline solution which contained a protein (human IgG) at 100 μg/ml. The grid was then transferred to an aqueous solution of a monoclonal antibody, anti-DNP IgG or anti DNP IgE and allowed to incubate for 1 hour.

The degree of 2-D high density binding of IgG and IgE directly measures the fraction of the lipid layer still on the grid; it indicates that the haptenated lipid is still on the surface. As a result of the improved stability of phospholipid bilayer, significantly improved 2-D crystallization of IgG and IgE was achieved as compared to the results obtained using the less stable phospholipid monolayer of Kornberg.

Although the above example is directed to only a few of the very many variables which can be utilized in the practice of the method of the present invention, it should be understood that the method of the present invention provides a much broader basis for growing a variety of ordered layers of macromolecules as shown in the description preceding this example.

What I claim as new and desire to secure by Letters Patent of the United States is:

1. A method for effecting the nucleation of macromolecules as an ordered monolayer on a hydrophilic region of a supported lipid polylayer having at least two hydrophilic regions and at least one interior lipophilic region comprising,
    (1) effecting contact between the macromolecules and a hydrophilic region of the lipid polylayer in an aqueous medium and
    (2) incubating the resulting mixture for a time sufficient to allow for the ordering of such macromolecules, where the lipid polylayer is anchored onto a supporting hydrophilic substrate through one of its hydrophilic regions.

2. A method in accordance with claim 1, where the lipid polylayer is a lipid bilayer.

3. A method in accordance with claim 1, where the lipid polylayer is formed from N-dinitrophenyl phosphatidylethanolamine.

4. A method in accordance with claim 1, where the lipid polylayer is formed from N-dinitrophenylaminocaproylphosphatidylethanolamine.

5. A method in accordance with claim 1, where the macromolecules are polyamino acids.

6. A method in accordance with claim 1, where the macromolecule is an antibody.

* * * * *